United States Patent [19]

Slayman

[11] Plant 4,274

[45] Jul. 4, 1978

[54] POMEGRANATE TREE

[76] Inventor: M. Dwight Slayman, 30701 Fairgreens West, Laguna Niguel, Calif. 92677

[21] Appl. No.: 793,181

[22] Filed: May 2, 1977

[51] Int. Cl.[2] ..... A01H 5/03
[52] U.S. Cl. ..... Plt./33
[58] Field of Search ..... Plt./33

*Primary Examiner*—Robert E. Bagwill
*Attorney, Agent, or Firm*—James W. Lucas

[57] ABSTRACT

A pomegranate tree of a new and distinct variety, with about a 10 day shorter period between the appearance of blossoms and the ripening of the fruit than is the case with the "Wonderful" variety. The fruit has a more pleasing shade of red than the "Granada", and the pulp has a slightly less acid taste than the "Wonderful".

4 Drawing Figures

The present invention concerns pomegranate trees and relates in particular to a new and distinct variety thereof characterized by regular bearing of relatively early ripening fruit of a pleasing red color and having a mildly acid pulp with rather tart seeds enclosed therein.

Reference is made to U.S. Plant Pat. No. 2,618 issued to Mitchell J. Slayman for a tree bearing an early ripening type of pomegranate, referred to in the industry as the Granada. The instant variety blossoms at about the same time as both the Granada and the Wonderful (unpatented) trees. The Granada ripens about a month earlier than the Wonderful. In contrast, the instant variety ripens about ten days earlier than the Wonderful, and combines the characteristic lustre of the Wonderful with a more pleasing shade of red than the Granada. The pulp has a mildly acid taste, slightly less than the Wonderful.

I discovered the present variety of pomegranate tree as a sport of the Wonderful variety, growing on the ranch at 1487 W. Linda Vista Dr. in Porterville, Calif. The sport was located adjacent other trees showing the normal Wonderful characteristics. The new tree is nearly identical with the Wonderful, except that the earlier ripening of the fruit brings out the color earlier, which color is in itself more attractive.

The unusual nature of the sport tree was first recognized in 1969. Not only did the fruit ripen earlier than the Wonderful variety, but the red coloration appeared about 2 weeks before ripening. The pulp was of about the same color and appearance as the Wonderful, but had a slightly less tart taste and lower acid content. The fruit had about the same lustre as the Wonderful and the color, compared to the "blood red" color of the Granada, was more of a "cherry red" hue.

In 1970, cuttings were rooted from the recognized sport on our grove at Avenue 196 and Road 196 in Strathmore, Calif., and developed into trees. These trees were substantially identical in appearance to the parent tree. The fruit already had a pleasing red color by the end of August, and was ready for picking by 10 September, about 10 days earlier than the other Wonderful fruit. All characteristics of the sport were identically reproduced in about four acres of the trees developed from the cuttings.

The accompanying drawings are color photographs, and show (1) several specimens of the mature fruit on the subject tree, (2) a mature fruit (right) next to a typical Wonderful fruit picked at exactly the same time (left) and (3) a sectioned ripened fruit showing the pulp and seeds.

Referring now in greater detail to this new and distinct variety of pomegranate tree, the following observations have been made at our grove in Strathmore, Calif., and comprise a brief outline description thereof. Colors are described with reference to the Munsell Book of Color (Munsell Color Co., Inc., Baltimore, Md.).

TREE

With regard to leaves, branches and tree size, the new variety of pomegranate tree is substantially identical to the Wonderful variety from which it is a sport.

Flowers bloom approximately the same time as the Wonderful variety and are about the same size and color.

FRUIT

Form: Approximate spherical shape typical of pomegranate fruit, with a characteristic crown opposite the stem end.

Size: About the same size as that of the Wonderful variety.

Skin:

*Color when green.*—Body of fruit is light to medium green, with a crown of about the same color (2.5 GY, 6/8). Body of fruit gradually changes color as it ripens, becoming a light cherry red (7.5 R, 5/12) approximately 2 weeks before maturity.

*Color when ripe.*—Medium to dark cherry red (7.5 R, 4/14) at maturity, with a lustre similar to that of the Wonderful.

Pulp: Mildly acid taste, but slightly less tart than the Wonderful variety.

Maturity date: Ripens about 10 days ahead of the Wonderful variety, or approximately 10 September in the San Joaquin Valley of Calif. As specified by the State Dept. of Agriculture, maturity occurs when the acid content drops below 1.85%. The Wonderful variety normally reaches this condition about 20 September.

The new variety of pomegranate tree has been described in terms of its characteristics when grown in the San Joaquin Valley of Calif. but variations due to fertilization, growing conditions in general, pest control and pruning can be expected to occur.

Having herein described and illustrated my new variety of pomegranate tree, what I claim as new and desire to be secured by Letters Patent is:

1. A new and distinct variety of pomegranate tree substantially as described and illustrated, said tree resembling the Wonderful (unpatented) pomegranate tree in appearance and blossoms, but being distinguished therefrom by its regular bearing of fruit which ripens about 10 days earlier than that of the Wonderful variety, is of a more pleasing cherry red color and is slightly less tart in flavor.

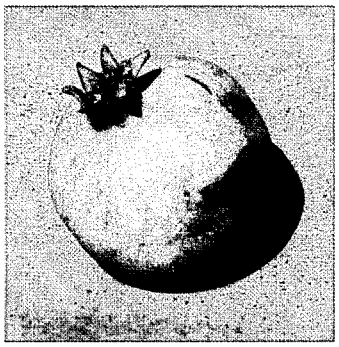
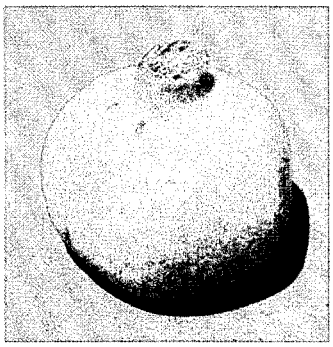
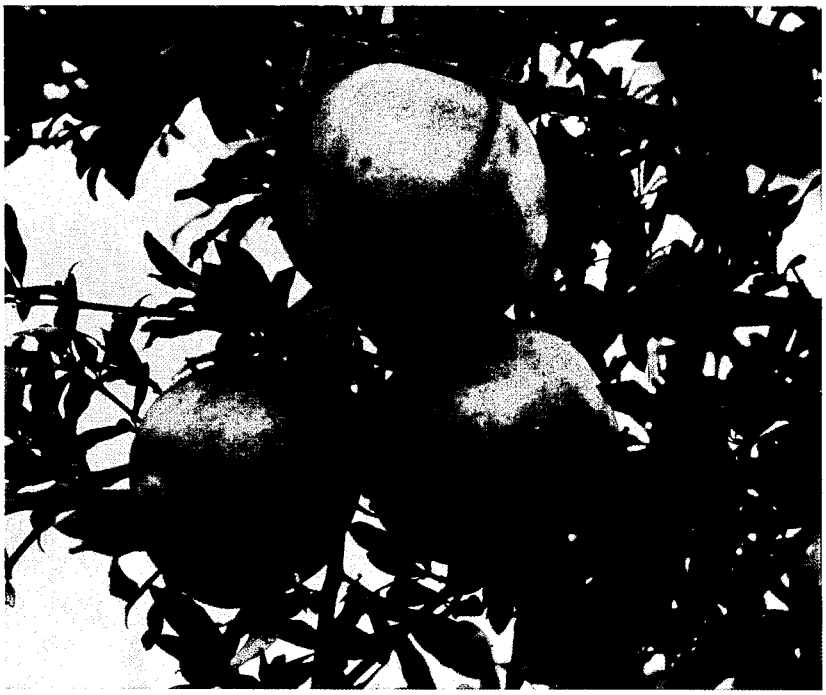
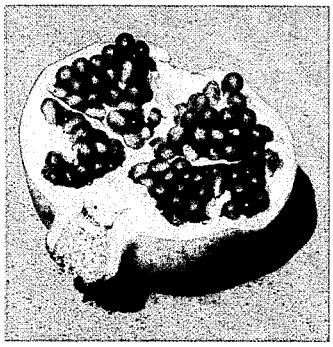

* * * * *